United States Patent [19]

Meserve

[11] Plant 4,803

[45] Jan. 19, 1982

[54] ILEX PLANT—MESDOB VARIETY

[75] Inventor: Kathleen K. Meserve, St. James, N.Y.

[73] Assignee: The Conard-Pyle Company, West Grove, Pa.

[21] Appl. No.: 163,272

[22] Filed: Jun. 26, 1980

[51] Int. Cl.[3] ..... A01H 5/00

[52] U.S. Cl. ..... Plt./65

[58] Field of Search ..... Plt./65

*Primary Examiner*—James R. Feyrer

*Attorney, Agent, or Firm*—Burns, Doane, Swecker & Mathis

[57] ABSTRACT

A new and distinct variety of Ilex which originated as a cross-pollination of *Ilex rugosa* and *Ilex cornuta* is provided. The new variety possesses attractive medium green foliage, produces an abundance of staminate flowers, and exhibits a compact and symmetrical growth habit and good tolerance to cold.

2 Drawing Figures

SUMMARY OF THE INVENTION

My invention relates to a new, distinctive and useful form of Ilex originated by me by crossing an unnamed and unpatented seedling known botanically as *Ilex rugosa* with an unnamed and unpatented seedling known botanically as *Ilex cornuta.*

The object of my breeding was to create a hardy, compact and versatile shrub of attractive appearance which combined the hardiness of *Ilex rugosa* with the beauty and versatility of *Ilex cornuta.* This objective was successfully achieved, and the new variety exhibits a combination of characteristics which distinguish it from all other forms of Ilex of which I am aware.

The following combination of characteristics is exhibited by the new variety:

(a) a well-branched, symmetrical, compact, vigorous habit of growth which is well-adapted to a wide range of landscape uses, (b) an abundance of staminate flowers which appear in spring and which produce the pollen necessary for fertilizing the pistilate flower of other varieties of the same cross, as well as varieties of *Ilex* × *meserveae* and some other forms of Ilex, (c) the ability to be sheared and trimmed to be kept within prescribed limits or shaped to a particular form, (d) cold tolerance which is superior to the species *Ilex cornuta* as well as most cultivars of that species, as evidenced by the fact that the present variety has survived with no visible damage temperatures of −15° F., whereas the species *Ilex cornuta* and most of its cultivars are listed as hardy to 0° F., (e) good heat tolerance which is characteristic of *Ilex cornuta* and which is much improved over *Ilex rugosa,* and, (f) green, semi-glossy foliage which is less quadrangular in shape as well as less glossy in appearance than *Ilex cornuta.*

In excess of fifty percent of two year old container grown plants of the present variety measure approximately 15 to 18 inches in height and breadth when grown at West Grove, Pa.

Asexual reproduction, by cuttings, of my new plant has been accomplished at St. James, N.Y., and at West Grove, Pa. Succeeding propagations have shown the unique combination of characteristics are fully established and transmitted to successive generations.

The new variety has been named the Mesdob variety.

BRIEF DESCRIPTION OF THE PHOTOGRAPHS

The accompanying photographs show typical specimens of my new variety of Ilex during late May as depicted in color as true as is reasonably possible to make the same in color photographs of this character. The specimens in the photographs were grown in the ground at West Grove, Pa.

FIG. 1 shows a typical four year old plant of the present variety.

FIG. 2 shows typical branches and leaves of the present variety. The current year's growth and the prior year's growth are apparent on the branches. The upper and lower surfaces of the leaves are shown.

DETAILED DESCRIPTION

Figure 1:
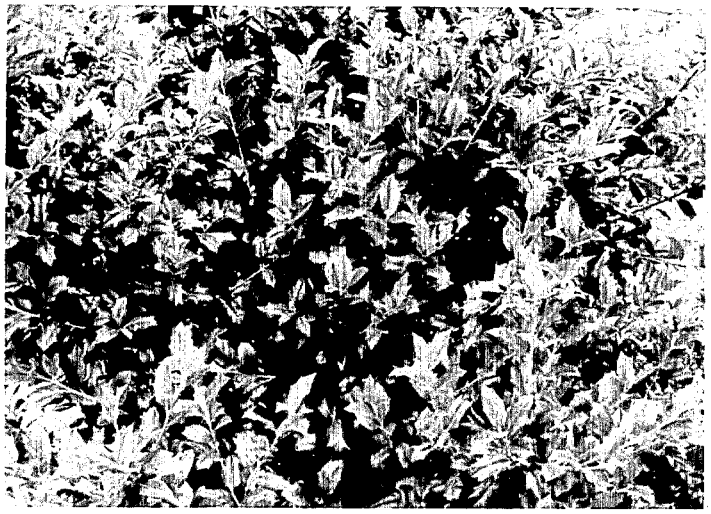
Figure 2:
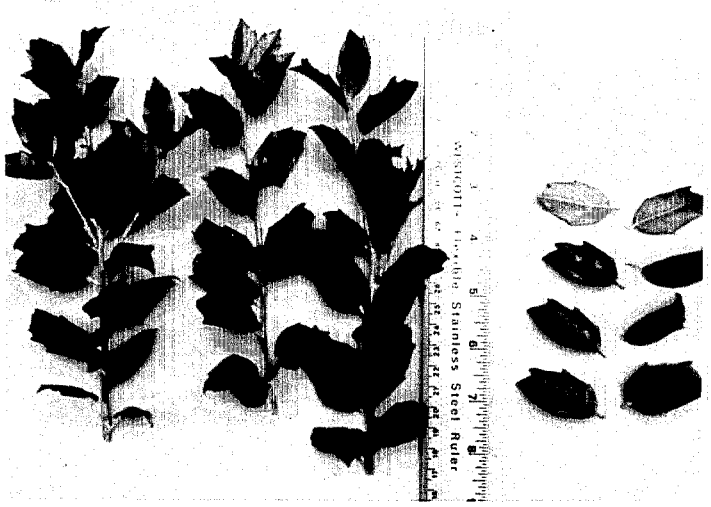

The following is a detailed description of my new variety made in late May from four year old plants growing in the ground at West Grove, Pa. Color terminology is made in accordance with The R.H.S. Colour Chart of The Royal Horticultural Society, London, England.

Parentage: *Ilex rugosa* seedling × *Ilex cornuta* seedling.

Foliage:

*Type.*—Evergreen. Leaves mostly eliptic in shape, with some leaves oblong. Apex acute, base obtuse. Leaves have from two to three pairs of prominent spines, with a single spine at the apex.

*Size.*—Mature leaves on main stems (measurements to tips of spines) — length from approximately 3.5 to 6.0 cm., with an average of approximately 5.1 cm.; width from approximately 2.1 to 3.5 cm. with an average of approximately 3.1 cm. Petiole length averages 0.6 cm.

*Color.*—Mature leaves, upper surface — closest to, but slightly yellower than Green Group 135A; under surface — Green Group 143B. Leaves are semi-glossy. Immature leaves, upper surface — closest to, but slightly yellower than Green Group 141B; underside — Green Group 143B.

Stems:

*Color.*—Green Group 143B.

Flowers: Flowers are substantially identical to those of *Ilex cornuta.*

I claim:

1. A new and distinct variety of Ilex, substantially as herein shown and described, characterized particularly as to novelty by the unique combination of:

(a) a well-branched, symmetrical, compact, vigorous habit of growth which is well-adapted to a wide range of landscape uses, (b) an abundance of staminate flowers which appear in spring and which produce the pollen necessary for fertilizing the pistilate flower of other varieties of the same cross, as well as varieties of *Ilex* × *merserveae* and some other forms of Ilex, (c) the ability to be sheared and trimmed to be kept within prescribed limits or shaped to a particular form, (d) cold tolerance which is superior to the species *Ilex cornuta* as well as most cultivars of that species, as evidenced by the fact that the present variety has survived with no visible damage temperatures of −15° F., whereas the species *Ilex cornuta* and most of its cultivars are listed as hardy to 0° F., (e) good heat tolerance which is characteristic of *Ilex cornuta* and which is much improved over *Ilex rugosa,* and, (f) green, semi-glossy foliage which is less quadrangular in shape as well as less glossy in appearance than *Ilex cornuta.*

* * * * *